US008155362B2

(12) United States Patent
Chris et al.

(10) Patent No.: US 8,155,362 B2
(45) Date of Patent: Apr. 10, 2012

(54) WIRELESS LISTENING SYSTEM

(75) Inventors: Dutton Chris, Chattanooga, TN (US); Corina Sandulescu, Chattanooga, TN (US); Ronald Webber, Chattanooga, TN (US); David G Lashley, Cartersville, GA (US)

(73) Assignee: Plantronics, Inc., Santa Cruz, CA (US)

( * ) Notice: Subject to any disclaimer, the term of this patent is extended or adjusted under 35 U.S.C. 154(b) by 1076 days.

(21) Appl. No.: 11/998,333

(22) Filed: Nov. 29, 2007

(65) Prior Publication Data

US 2009/0141918 A1 Jun. 4, 2009

(51) Int. Cl.

| | |
|---|---|
| ***H04R 9/06*** | (2006.01) |
| ***H04R 25/00*** | (2006.01) |
| ***H04R 27/00*** | (2006.01) |
| ***H04H 40/54*** | (2008.01) |
| ***A61B 7/04*** | (2006.01) |
| ***H04B 15/00*** | (2006.01) |

(52) U.S. Cl. ............ 381/334; 381/10; 381/67; 381/312; 381/82; 381/94.3

(58) Field of Classification Search .................. 381/334, 381/315, 312–314, 23.1, 82, 120, 7, 10, 67, 381/80, 94.3

See application file for complete search history.

(56) References Cited

U.S. PATENT DOCUMENTS

| | | | | |
|---|---|---|---|---|
| 5,095,382 | A * | 3/1992 | Abe | 398/202 |
| 5,642,426 | A * | 6/1997 | Neuman et al. | 381/312 |
| 5,768,397 | A * | 6/1998 | Fazio | 381/312 |
| 6,370,401 | B1 * | 4/2002 | Baranowski et al. | 455/569.1 |
| 6,735,306 | B1 * | 5/2004 | Heinz | 379/430 |
| 6,847,725 | B1 * | 1/2005 | Neuman et al. | 381/383 |
| 7,181,024 | B1 * | 2/2007 | Oba et al. | 381/77 |
| 7,369,670 | B2 * | 5/2008 | Haussmann | 381/322 |
| 7,873,177 | B2 * | 1/2011 | Okamura et al. | 381/374 |
| 2004/0258253 | A1 * | 12/2004 | Wurtz | 381/71.6 |
| 2005/0013447 | A1 * | 1/2005 | Crump et al. | 381/71.6 |
| 2008/0165994 | A1 * | 7/2008 | Caren et al. | 381/312 |
| 2008/0232623 | A1 * | 9/2008 | Solum et al. | 381/323 |

* cited by examiner

*Primary Examiner* — Anh Mai
*Assistant Examiner* — Mangtin Lian
(74) *Attorney, Agent, or Firm* — Donald C. Lawrence; Andre Tacdiran

(57) ABSTRACT

A wireless listening system includes a base operable to receive an electrical signal corresponding to an audio signal, including the ring of an incoming telephone call, up-convert the audio signal to an infrared signal, and transmit the infrared audio signal wirelessly therefrom, and a wireless headset operable to selectably receive either the infrared audio signal transmitted by the base, or an infrared signal corresponding to an audio signal transmitted by a public address system, down-convert the received signal back into the audio signal, and audibly reproduce the audio signal to a wearer of the headset. The system enables a hearing impaired listeners to enjoy their favorite audio programs without disturbing nearby persons with normal hearing and without missing an incoming telephone call, and is also compatible with public IR PA systems currently used to assist the hearing impaired community.

18 Claims, 6 Drawing Sheets

WIRELESS LISTENING SYSTEM

BACKGROUND

This disclosure relates to wireless communication systems in general, and in particular, to wireless listening systems for the hard-of-hearing that use infrared signals to enable such users to hear and better understand the sound from home stereos, televisions, computers, public address systems, theaters and the like, while also providing the ability to alert the user to incoming telephone calls.

Nearly 34 million Americans are affected by a hearing impairment that is sufficiently profound as to prevent them from enjoying television, music and other audio program broadcasts. In addition to private settings in which the hard-of-hearing may not be able to hear sound broadcasts adequately, this segment of the population may also be excluded from hearing in public meetings, church services or theater events and the like.

There are currently a number of personal sound amplification devices on the market that amplify sounds from stereos, televisions and computers through the standard 2.3 MHz and 2.8 MHz infrared (IR) communication protocols. However, these devices are not compatible with the standard 95 KHz public broadcast protocol. Moreover, the devices that are compatible with the 95 KHz public broadcast standard are not compatible with the 2.3 MHz and 2.8 MHz systems. Moreover, there are currently no IR listening devices on the market that are capable of being connected to a telephone line and that can give notification to a user of incoming telephone calls while they are listening to an audio program with the devices.

Accordingly, there is a need on the part of hard-of-hearing users for a wireless listening system that enables the user not only to hear and better understand sounds broadcast by both private and public sources, but that also notifies the user of incoming telephone calls while listening to an audio program.

BRIEF SUMMARY

In accordance with the exemplary embodiments thereof described herein, a wireless listening system is disclosed that enables a hard-of-hearing user to experience amplified, enhanced sound reproduction from televisions, stereos, computers and other electrical appliances using the standard 2.3 and 2.8 MHz IR communication protocols, and also to use the wireless headset of the system in public settings, such as, e.g., city council meetings, school auditoriums, movie theaters and churches, using an integral 95 KHz infrared communication protocol, and further, to be notified of incoming telephone calls while using the system.

In one exemplary embodiment, the system comprises a base that is operable to receive an electrical signal corresponding to an audio signal, including a ring signal corresponding to an incoming telephone call, up-convert the audio signal to an infrared signal, and transmit the infrared audio, signal wirelessly therefrom, and a wireless headset that is operable to selectably receive either the infrared audio signal transmitted by the base, or alternatively, an infrared signal corresponding to an audio signal transmitted by a public address system, down-convert the received signal back into the audio signal, and audibly reproduce the audio signal to a wearer of the headset, including the production of an audible notification of the incoming telephone call.

In another exemplary embodiment, the base frequency modulates a carrier signal with the audio and incoming telephone call signals, and the audio signal may comprise a stereo signal, i.e., separate left and right sound channels, and the base and the headset are respectively operative to receive, up-convert and transmit, and to receive, down-convert, and audibly reproduce each of the channels to the wearer simultaneously and separately from each other. The left and right channels of the audio program may be respectively transmitted by the base and received by the headset on different carrier frequencies, which in one particular exemplary embodiment may comprise carrier frequencies of 2.3 MHz and 2.8 MHz, respectively. The headset of the system is also capable of receiving an infrared audio signal transmitted by the public address source on a carrier frequency of 95 KHz.

A better understanding of the above and many other features and advantages of the novel wireless listening system of the present invention may be obtained from a consideration of the detailed description of some exemplary embodiments thereof below, particularly if such consideration is made in conjunction with the appended drawings, wherein like reference numerals are used to identify like elements illustrated in one or more of the figures thereof.

DETAILED DESCRIPTION

Figure 1:
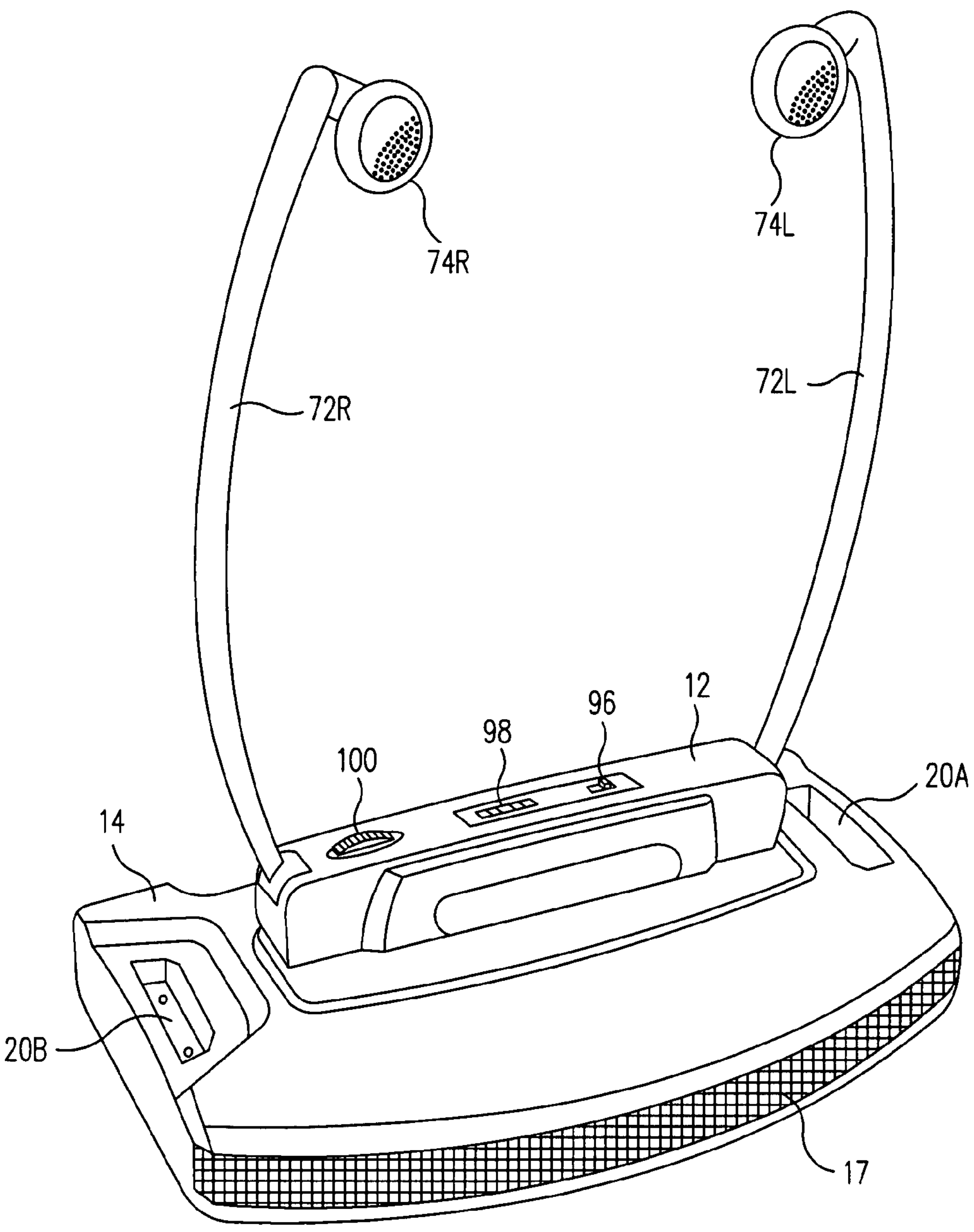
FIG. 1 is an upper, right side and front perspective view of an exemplary embodiment of a wireless listening system in accordance with the present invention, showing a wireless headset unit of the system docked in an associated base unit thereof.

FIG. 1 is an upper, right side and front perspective view of an exemplary embodiment of a wireless listening system 10 in accordance with the present invention, showing a wireless headset unit 12 of the system docked in an associated base unit 14 thereof. The listening system 10 is intended for the hard-of-hearing, and accordingly, the amplified headset 12 and a base 14 are specifically designed for transmission and reception of infrared signals for the purpose of reproducing sound generated from home stereos, televisions, computers, and the like, as well as public address systems, such as theaters, auditoriums and other public sound sources, while also providing the ability to alert the user to an incoming telephone call. The system is thus designed as a consumer electronic solution for those who experience a mild-to-severe hearing loss who wish to experience both public and private sound broadcasts.

Figure 2:
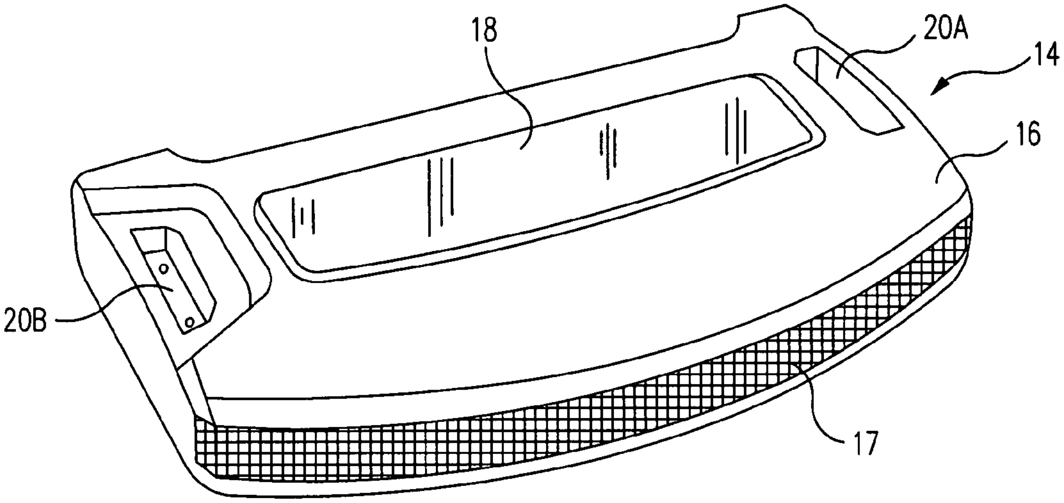
FIG. 2 is an upper right side and front perspective view of the base unit of the exemplary system.

The base unit 14 of the exemplary system 10 is illustrated in the upper right and front side perspective view of FIG. 2, and comprises a low-profile housing 16 adapted to sit atop a TV, radio, stereo set, book shelf or the like, and to radiate IR signals forwardly, across a substantially wide angle of transmission, and towards a hard-of-hearing listener wearing the headset 12 of the system, as described in more detail below. The base includes a receptacle 18 adapted to receive the headset in a complementary, plug-in engagement, as illustrated in FIG. 1, and as discussed below, a battery charger that is operative to charge a rechargeable battery contained in the headset while the base and the headset are engaged with each other. The base additionally includes a pair of separate spare battery charging receptacles 20A and 20B, each adapted to receive and continuously charge a spare battery (not illustrated) for the headset. This arrangement ensures that the headset of the system will always have an ample source of power available, even with extended use away from home and remote from the base.

Figure 4:
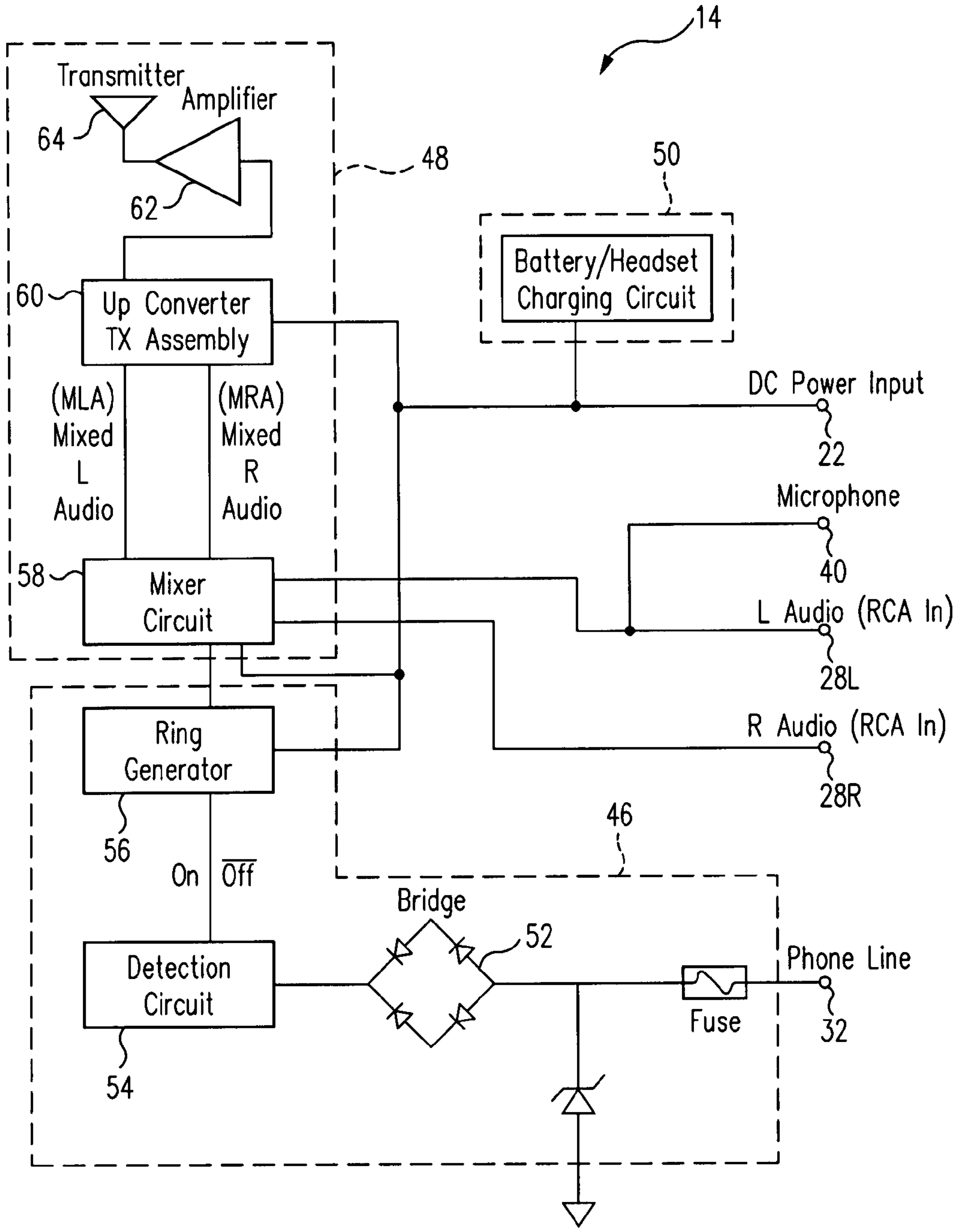
FIG. 4 is a functional block diagram of the base unit of the system.
Figure 6:
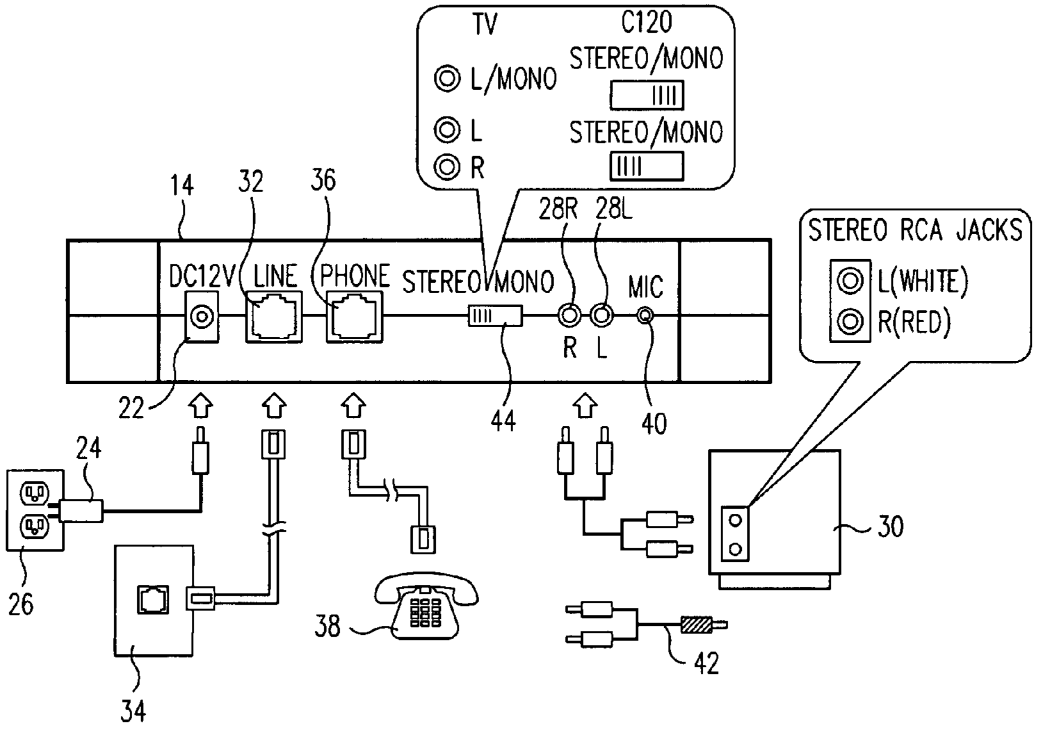
FIG. 6 is a rear elevation view of the base of the system showing various signal connection inputs to the base.

FIG. 4 is a functional block diagram of the base unit 14 of the system 10, and FIG. 6 is a schematic rear elevation view of the base showing the various signal connection inputs thereto. As illustrated in the particular exemplary embodiment of FIGS. 4 and 6, the signal inputs include a DC power input 22 from, e.g., a transformer 24 that plugs into a conventional AC wall power receptacle 26, Left and Right audio channel electrical signal inputs 28L and 28R (e.g., RCA jacks), that are output by an electrical appliance 30, such as a television, stereo or computer, and a telephone "Line" input 32, e.g., a Public Switched Telephone Network (PSTN) Line input, fed from, e.g., a conventional RJ11 telephone wall jack 34. The base also includes an RJ11 jack 36 that enables a standard telephone set 38 to be coupled to the Line input through the base.

As illustrated in FIG. 6, the base 14 also includes a socket 40 for coupling a microphone (not illustrated) into the base, which is provided to make the system 10 "backwards-compatible" to older electrical appliances 30, such as a TV, that lack audio output jacks that enable coupling of its audio program electrical signals directly to the base. By connecting the microphone to the base and then disposing the microphone adjacent to the loudspeaker of the appliance, the microphone serves to transform the audio signal from the speaker into a corresponding electrical signal that is transmitted to the headset 12 in the same manner that the Left and Right channel and incoming telephone call notification signals are transmitted thereto, as described below.

The exemplary system 10 may also include an adapter cable 42 that enables a monophonic audio source (not illustrated) to be coupled to the Left and Right channel inputs 28L and 28R of the base 14, as well as a "Stereo/Mono" selector switch 44 that enables the operation of the base to be switched between a monophonic mode, in which the audio program signal input to the Left channel input 18L is transmitted by the base on both transmit channels, and a stereophonic mode, in which each of the Left and Right channels of the audio program are transmitted on a separate channel, as described in more detail below.

As illustrated in the functional block diagram of FIG. 4, the base 14 comprises three main functional sections of components, viz., an incoming telephone call notification signal generator 46, an audio signal mixing, up-converting and transmitting section 48, and a headset battery charging section 50. The incoming telephone call notification signal generator comprises a bridge 52 for rectifying the incoming telephone "ring" signal from the telephone Line input 32, a detection circuit 54 for detecting the ring signal, and a ring generator 56 that generates a telephone ringing signal in response to an incoming telephone call and outputs it to the audio signal mixing, up-converting and transmitting section 48 of the base.

Figure 8:
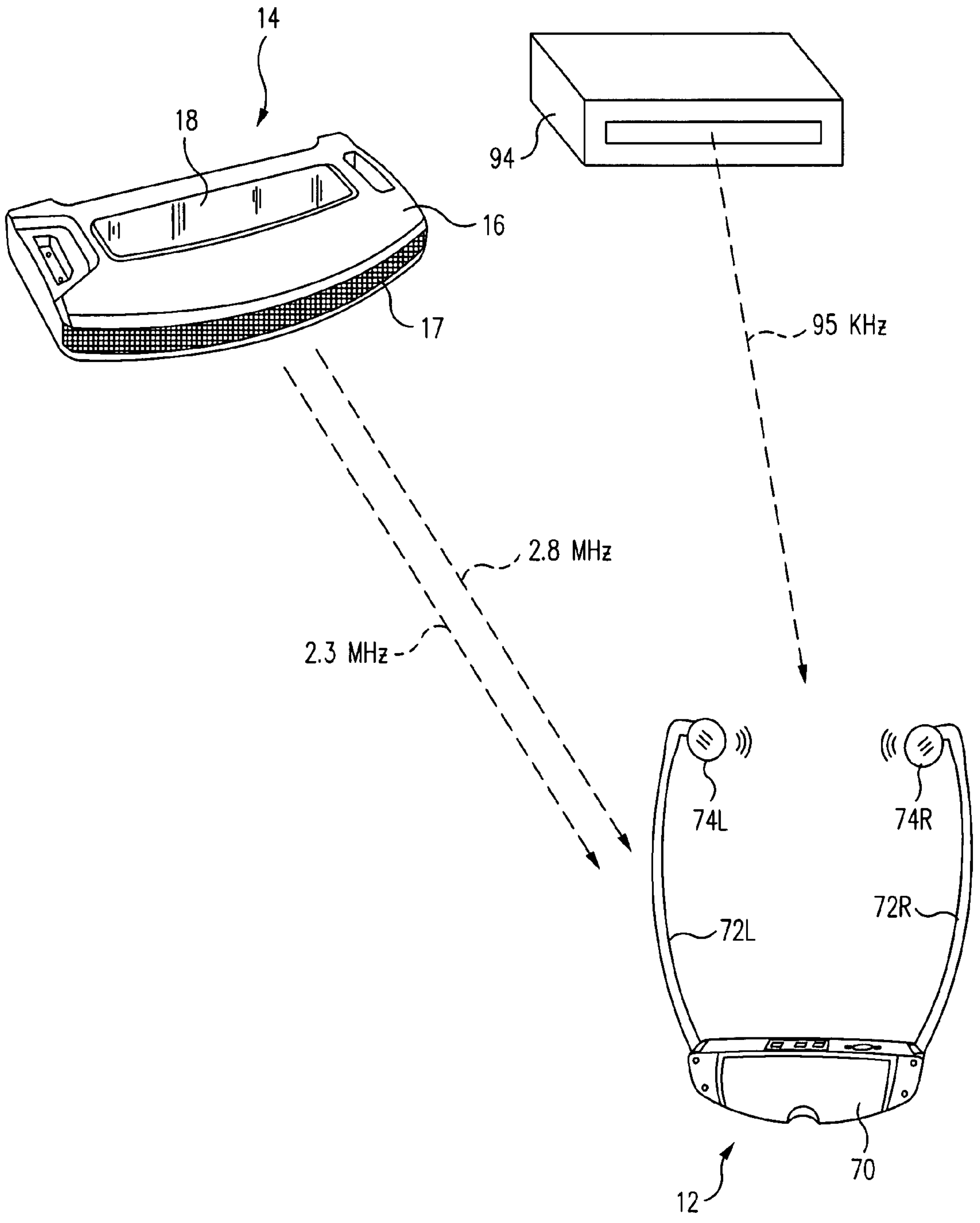

The audio mixing, up-converting and transmitting section 48 of the base 14 comprises a signal mixer 58, a signal up-converter 60, a transmission amplifier 62, and a transmitter 64 for radiating the transmitted signals from the base. The audio section is operable to receive the respective electrical signals corresponding to the Left and Right audio channels signals, the incoming telephone call notification signal, and selectably, the microphone input signal, and to then up-convert the respective audio signals to infrared signals and transmit the infrared audio signals wirelessly from the base 14 to the wireless headset 12, as illustrated in FIG. 8.

In the particular exemplary embodiment described and illustrated, the audio section 48 of the base 14 frequency modulates two separate infrared carrier signals at 2.3 MHz and 2.8 MHz, respectively, with the audio and incoming telephone call signals, and outputs them both simultaneously from the base 14 via the amplifier 62 and transmitter 64. Thus, each of the Left and Right channels of a stereo audio program is carried on a separate channel, each having a frequency response of 20 Hz-20 KHz, for maximum channel separation and sound fidelity. However, as those of skill in the art will appreciate, other modulation and/or multiplexing techniques can also be used. The transmitter 64 comprises a plurality of light emitting diodes (LEDs) operating at a wavelength of, e.g., 850 nm, which are arrayed behind a IR-transparent front panel 17 (see FIG. 1) of the base, to radiate the up-converted audio signals forwardly, across a wide angle of transmission, over a line-of-sight range of up to 30 ft., and to the headset 12 of the system.

As a power-saving feature, the base 14 also includes a timer circuit that deactivates the base, except for the headset battery charging section 50 thereof described below, after a predetermined period of time during which no audio signal is input to the base, and that automatically reactivates the base when such an audio signal is input thereto.

As discussed above, the battery charging section 50 of the base 14 comprises circuitry adapted to automatically recharge the battery of the headset 12 while the headset is plugged into the complementary receptacle 18 of the base, as illustrated in FIG. 1, as well as to continuously charge a pair of spare headset batteries (not illustrated) respectively received in the spare battery charging receptacles 20A and 20B of the base. This arrangement enables the user to take two fully charged backup batteries, as well as the one contained in the headset, for extended periods of use remote from the base.

Figure 3:
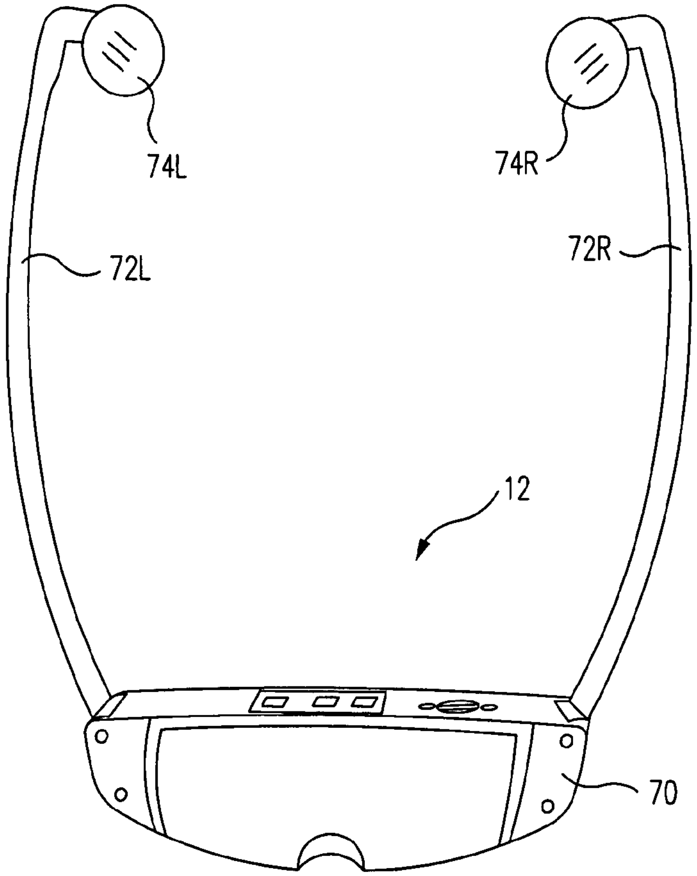
FIG. 3 is an upper rear perspective view of the wireless headset unit of the system.
Figure 5:
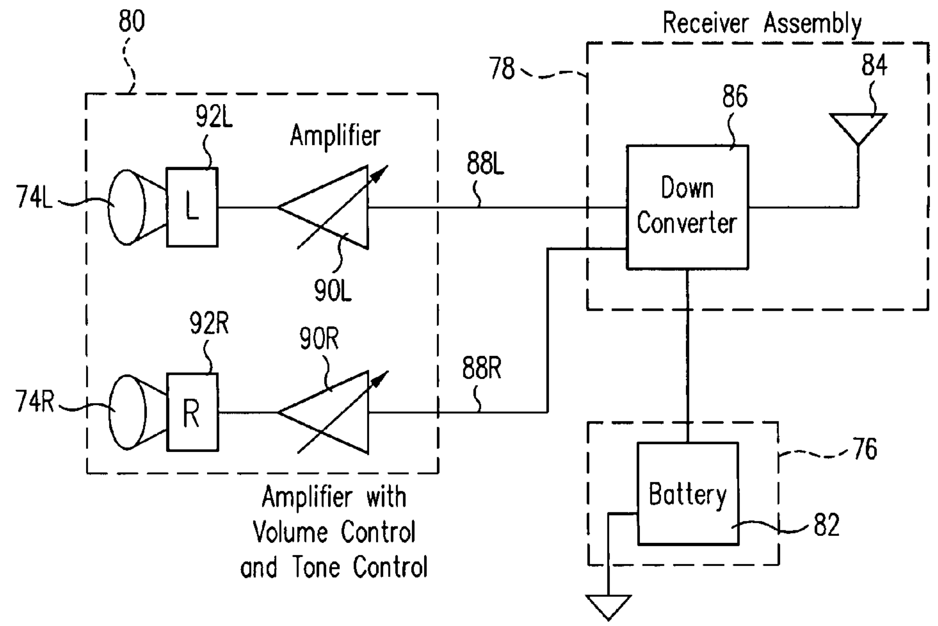
FIG. 5 is a functional block diagram of the headset unit of the system.
Figure 7:
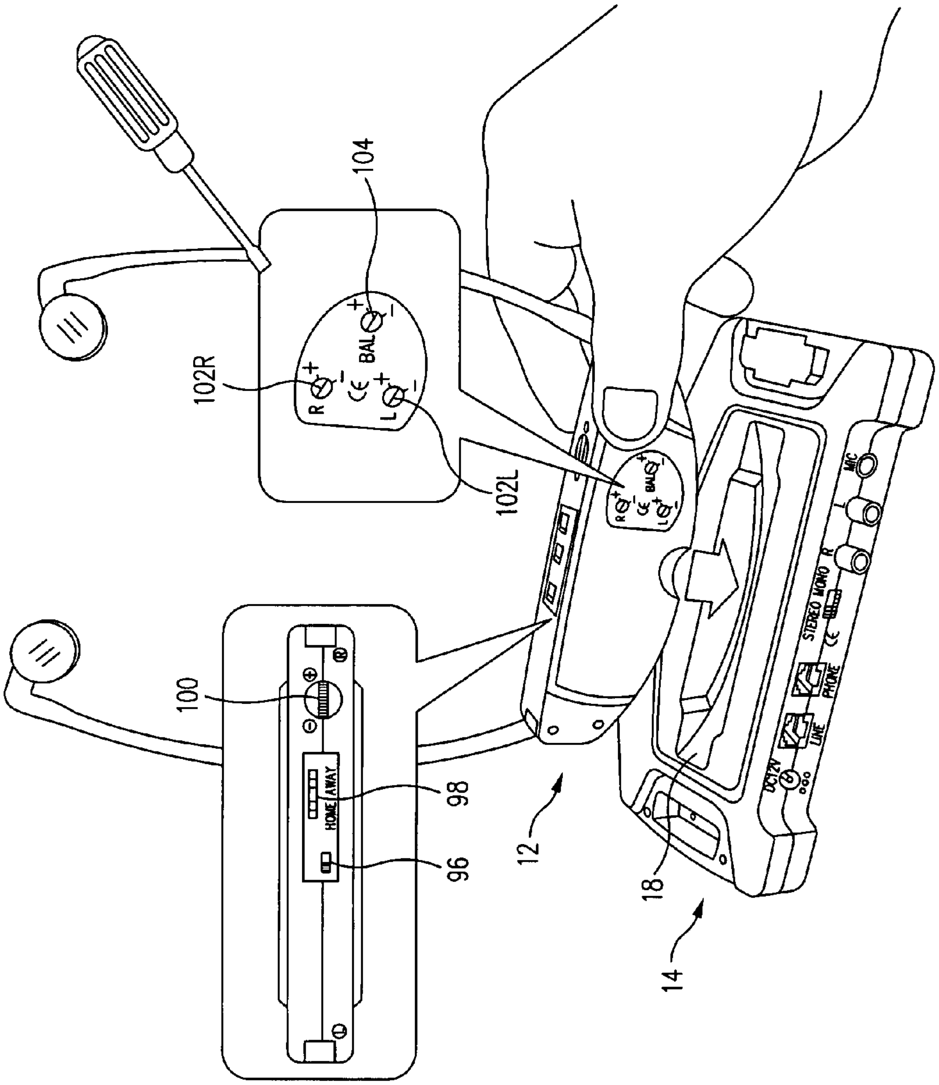
FIG. 7 is a top, front perspective view of the base and headset units showing the adjustment of various controls thereof; and, FIG. 8 is a perspective view of the base and headset units of the listening system shown separated from each other by a distance, illustrating the base unit and a public broadcasting transmitter wirelessly transmitting respective IR signals to the headset unit of the system.

FIG. 3 is an upper rear perspective view of the wireless headset unit 12 of the listening system 10, and FIG. 5 is a functional block diagram thereof. As illustrated in FIG. 3, the headset comprises a main body 70 and a pair of stethoscope-like earpieces 72L and 72R, each of which is equipped with a respective ear bud 74L and 74R adapted to be inserted into a respective one of the wearer's left and right ears. In use, the main body of the headset hangs down, pendant-like, from the ear pieces and below the wearer's chin. As a power-conserving feature, the two earpieces are biased toward each other, e.g., with a spring mechanism, and are operative to automatically activate the headset when spread apart from each other, i.e., while the headset is being worn, and to automatically deactivate the headset when biased together, e.g., when the wearer takes the headset off and inserts it into the charging receptacle 18 of the base 14, as illustrated in FIG. 7.

As illustrated in FIG. 5, the headset 12 comprises three main functional sections, a power supply section 76, a receiver and down-converter section 78, and a signal transforming and amplification section 80. As discussed above, the power supply section comprises a rechargeable battery 82. In one preferred exemplary embodiment, the battery comprises a nickel metal hydride (NiMH) battery having a minimum (per charge) battery life of about 6 hours.

The receiver and down-converter section 78 of the headset 12 comprises an infrared light detector 84 for detecting infrared light signals transmitted from both the base unit 14 and other public address transmitters, as described below, and a signal down-converter section 86. The detector outputs the infrared signals received to the down-converter, which functions to demodulate the audio signals from the infrared signals into two, separate, left and right audio-frequency signals 88L and 88R that are then input to the transforming and amplification section 80. The transforming and amplification section comprises a pair of adjustable-gain amplifiers 90L and 90R and an associated pair of electro-acoustic transducers, or earphones 92L and 92R that respectively amplify and transform the left and right audio channel electrical signals 88L and 88R into acoustic sound signals that are respectively input into the left and right ears of the listener via the respective earpieces 72L, 72R and ear buds 74L, 74R of the headset. The amplifiers are capable of adjustably applying a minimum of 50 dB and 120 dB SPL of amplification to the audio signal reproduced to the ears of the listener.

In addition to its capability of receiving and down-converting the infrared signals respectively transmitted by the base 14 on the two 2.3 and 2.8 MHz carrier frequencies, as discussed above, the receiver and down-converter section 78 of the headset 12 is also capable of receiving and down-converting infrared signals broadcast by a source 94 via the standard 95 KHz public address protocol used by many theaters, churches, and sponsors of pubic events, as illustrated schematically in FIG. 8. Thus, the wireless headset is not limited to use only in conjunction with the base unit 14, but also enables the hard-of-hearing user to better hear and understand audio programs in other environments that are equipped with a standard 95 MHz infrared sound transmission system.

FIG. 7 is a perspective view illustrating the headset 12 being plugged into the battery charging receptacle 18 of the base 14, and shows the adjustment of the various control features thereof. As illustrated in the left inset figure, the headset includes the following controls, located on the upper edge of the headset: An on/off switch 96 for manually activating/deactivating the headset, a "home/away" switch 98 that enables the user to select between use of the headset at home and in conjunction with the base, or alternatively, away from home and in conjunction with a public address broadcasting source 94, as discussed above, and a volume control switch 100. As illustrated in the right inset figure, the side surface of the headset also includes Left and Right channel gain controls 102L and 102R and a control 104 for adjusting the balance between the left and right channels, all of which, in the particular exemplary embodiment illustrated, are adjustable with a small screwdriver. Of course, other control placement and means of adjustment are also possible.

In accordance with the exemplary embodiments described herein, the novel listening system 10 of the present invention comprises an amplified, stereo, infrared (IR) listening system with telephone ring notification. It enables hard-of-hearing people with moderate to severe hearing loss to better hear and understand, e.g., television programs, without having to turn up the TV's sound volume and without disturbing the normal-hearing individuals in the household. The user can control the volume and tone of the program directly from the headset without affecting the TV settings. The listening system thus reduces background noise and overcomes distance by delivering audio directly from the sound source to the listener's ears.

Unlike conventional headsets, which only increase sound volume, the system 10 of the present invention improves the clarity of sound of, e.g., a TV program. This is crucial for many hard-of-hearing people who can hear sounds but have difficulty understanding certain sound frequencies. The system enhances a hard-of-hearing person's hearing experience not only while listening to television, but also while listening to stereo, movies or in other public environments that are equipped with a standard 95 MHz infrared sound transmission system.

The system 10 also provides incoming telephone call ring notification to the user while the user is listening to an audio program at home. When the telephone 38 rings, the base unit 14 transmits a corresponding IR "ringing" signal to the headset 12. In response, the headset emits a "beep" or other audible indicator to notify the wearer of the incoming call. This notification feature ensures that users will not miss a telephone call while they are listening to their favorite TV or other types of programs.

The system 10 is compatible with satellite, cable, digital, plasma and high definition (HD) television systems. The dual-channel 2.3 and 2.8 MHz carrier frequencies provide professional level stereo sound with minimum interference and cross-talk. The 95 kHz frequency capability enables the headset of the system to be compatible with the majority of public IR public address (PA) systems widely available to assist the hearing impaired community.

By now, those of skill in this art will appreciate that many modifications, substitutions and variations can be made in and to the novel wireless listening system of the present invention without departing from its spirit and scope. In light of this, the scope of the present invention should not be limited to that of the particular embodiments illustrated and described herein, as they are only exemplary in nature, but instead, should be fully commensurate with that of the claims appended hereafter and their functional equivalents.

What is claimed is:

1. A wireless listening system, comprising:

a base operable to receive an electrical signal corresponding to an audio signal, up-convert the audio signal to an infrared signal, and transmit the infrared audio signal wirelessly therefrom;

a wireless headset operable to selectably receive either the infrared audio signal transmitted by the base, or infrared signal corresponding to an audio signal transmitted by an infrared audio signal source, down-convert the received signal back into the audio signal, and audibly reproduce the audio signal to a wearer of the headset;

the base is further operable to detect an electrical signal corresponding to an incoming telephone call, up-convert the signal into an infrared incoming telephone call notification signal, and transmit the notification signal wirelessly therefrom; and the headset is further operable to receive the infrared notification signal transmitted by the base unit, down-convert the notification signal received into an incoming telephone call signal, and audibly reproduce the incoming telephone call signal to the wearer of the headset.

2. The system of claim 1, wherein the base is further operative to frequency modulate a carrier signal with the audio and incoming telephone call signals.

3. The system of claim 1, wherein the audio signal comprises separate left and right sound channels, and wherein the base and the headset are respectively operative to receive, up-convert and transmit, and to receive, down-convert, and audibly reproduce, each of the channels to the wearer simultaneously and separately from each other.

4. The system of claim 3, wherein the left and right channels of the audio program are respectively transmitted by the base and received by the headset on different carrier frequencies.

5. The system of claim 4, wherein one of the channels is transmitted on a carrier frequency of 2.3 MHz and the other channel is transmitted on a carrier frequency of 2.8 MHz.

6. The system of claim 1, wherein the infrared audio signal is respectively transmitted by the infrared audio signal source and received by the headset on a carrier frequency of 95 KHz.

7. The system of claim 1, wherein the headset is further operative to adjustably apply a minimum of 50 dB and 120 dB SPL of amplification to the audio signal reproduced to the wearer.

8. The system of claim 1, wherein:

the headset comprises a rechargeable battery;

the base comprises a battery charger;

the base is adapted to receive the headset in a complementary, plug-in engagement; and, the battery charger is operative to charge the battery while the base and the headset are engaged with each other.

9. The system of claim 1, wherein the headset comprises a pair of stethoscope ear-pieces that are biased toward each other, and are operative to activate the headset when spread apart and to deactivate the headset when biased together.

10. The system of claim 1, wherein the base comprises a timer that deactivates the base after a predetermined period of time during which no audio signal is received by the base, and that reactivates the base upon receipt of an audio signal.

11. The system of claim 1, further comprising a microphone operative to receive an acoustic signal from a sound source, convert the acoustic signal into an electrical audio signal and to input the audio signal into the base.

12. A method of enabling a hard-of-hearing person to better hear an audio program and without missing an incoming telephone call, the method comprising:

transforming the audio program into a corresponding electrical signal;

up-converting the electrical signal to an infrared signal; transmitting the infrared signal wirelessly to a wireless headset;

down-converting the infrared signal back into the electrical signal with the headset;

retransforming the electrical signal back into the audio program with the headset such that the program can be heard by the headset wearer;

wherein the audio program can include the ring signal of an incoming telephone call and an audio signal from an audio source;

the audio program comprises a stereo program; the up-converting comprises up-converting electrical signals respectively corresponding to left and right channels of the program to corresponding left and right infrared signals; and the transmitting comprises simultaneously transmitting the left and right infrared signals on respective ones of two different carrier signal frequencies.

13. The method of claim 12, wherein the carrier signal frequencies comprise 2.3 and 2.8 MHz signals, respectively.

14. The method of claim 12, wherein the transforming is effected by an electrical appliance or a telephone.

15. The method of claim 12, wherein the transforming, the up-converting and the transmitting is effected by an infrared audio signal source transmitting on a carrier signal frequency of 95 Khz.

16. The method of claim 12, wherein the transforming is effected by a microphone.

17. The method of claim 12, further comprising adjustably amplifying the retransformed electrical signal with the headset.

18. The method of claim 12, further comprising adjusting the balance between the left and right channels with the headset.

* * * * *